United States Patent
Carmel et al.

(10) Patent No.: US 6,921,398 B2
(45) Date of Patent: Jul. 26, 2005

(54) VIBRATING ELECTROSURGICAL ABLATOR

(75) Inventors: Yuval Carmel, Rockville, MD (US); Anatoly Shkvarunets, Rockville, MD (US); Robert A. Van Wyk, Largo, FL (US)

(73) Assignee: Electrosurgery Associates, LLC, Rockville, MD (US)

( * ) Notice: Subject to any disclaimer, the term of this patent is extended or adjusted under 35 U.S.C. 154(b) by 163 days.

(21) Appl. No.: 10/159,115

(22) Filed: Jun. 3, 2002

(65) Prior Publication Data

US 2002/0183742 A1 Dec. 5, 2002

Related U.S. Application Data

(60) Provisional application No. 60/295,541, filed on Jun. 4, 2001.

(51) Int. Cl.$^7$ .............................................. A61B 18/18
(52) U.S. Cl. .............................. 606/41; 607/105; 601/2
(58) Field of Search ............................. 606/41, 45, 46, 606/48–50; 607/101, 102, 104, 105; 601/2

(56) References Cited

U.S. PATENT DOCUMENTS

| | | | |
|---|---|---|---|
| 3,988,621 A | | 10/1976 | Nakayama et al. |
| 4,240,141 A | | 12/1980 | Vasiliev et al. |
| 4,282,763 A | | 8/1981 | Griebeler |
| 4,583,529 A | | 4/1986 | Briggs |
| 4,674,498 A | | 6/1987 | Stasz |
| 4,692,139 A | | 9/1987 | Stiles |
| 4,936,281 A | * | 6/1990 | Stasz .......................... 600/439 |
| 5,013,312 A | * | 5/1991 | Parins et al. .................. 606/37 |
| 5,282,799 A | * | 2/1994 | Rydell .......................... 606/48 |
| 5,334,183 A | | 8/1994 | Wuchinich |
| 5,465,171 A | | 11/1995 | Weber et al. |
| 5,918,354 A | | 7/1999 | Ikegami et al. |
| 6,024,742 A | | 2/2000 | Tu et al. |
| 6,050,993 A | * | 4/2000 | Tu et al. ........................ 606/41 |
| 6,142,996 A | | 11/2000 | Mirhashemi et al. |
| 6,165,206 A | * | 12/2000 | Tu ............................... 607/96 |
| 6,235,024 B1 | * | 5/2001 | Tu ............................... 606/41 |
| 6,335,586 B1 | | 1/2002 | Takeuchi et al. |
| 6,497,704 B2 | * | 12/2002 | Ein-Gal ....................... 606/41 |

FOREIGN PATENT DOCUMENTS

| | | | |
|---|---|---|---|
| GB | 2 327 352 A | | 1/1999 |
| GB | 2327352 | * | 1/1999 |

* cited by examiner

*Primary Examiner*—Michael Peffley
(74) *Attorney, Agent, or Firm*—Dickstein Shapiro Morin & Oshinsky LLP (57) ABSTRACT

A high efficiency electrosurgical ablator which is subjected to a fast and slight oscillatory motion during resection of tissue. The electrosurgical ablator is positioned in the proximity of the tissue to be treated in the presence of an electrically conductive fluid. A high frequency voltage is applied to the electrode of the ablator, and the ablator is subjected to a vibratory motion created by, for example, a mechanical or electromechanical oscillator or a piezoelectric element. The vibratory motion permits more tissue to become available in the destructive, sparking zone, thereby increasing the efficiency of operation.

8 Claims, 9 Drawing Sheets

VIBRATING ELECTROSURGICAL ABLATOR

The present application claims the benefit under 35 U.S.C. 119(e) of U.S. Provisional Application Ser. No. 60/295,541 filed on Jun. 4, 2001, the disclosure of which is incorporated by reference herein.

FIELD OF THE INVENTION

The present invention relates to the field of electrosurgery and, in particular, to electrosurgical devices and methods which employ high frequency voltage to cut, ablate or coagulate tissue.

BACKGROUND OF THE INVENTION

Electrosurgical procedures typically rely on the application of very high frequency or radio frequency (RF) electrical power to cut, ablate or coagulate tissue structures. For example, electrosurgery cutting entails heating tissue cells so rapidly that they explode into steam leaving a cavity in the cell matrix. When the electrode is moved and fresh tissue is contacted, new cells explode and the incisions is made. Such electrosurgical cutting involves the sparking of the current to the tissue, also known as the jumping of the RF current across an air gap to the tissue.

Radiofrequency electrodes employed in electrosurgical procedures are generally divided into two categories: monopolar devices and bipolar devices. In monopolar electrosurgical devices, the RF current generally flows from an exposed active electrode through the patient's body, to a passive or return current electrode that is externally attached to a suitable location on the patient's skin. In bipolar electrosurgical device, both the active and the return current electrodes are exposed and are typically in close proximity. The RF current flows from the active electrode to the return electrode through the tissue. Thus, in contrast with the monopolar electrosurgical devices, the return current path for a bipolar device does not pass through the patient.

Electrosurgery which takes place in a conductive fluid environment, such as inside of a joint or body cavity filled with, for instance, normalized saline solution, differs from that described previously in that current is conducted from the active electrode through the fluid to the return electrode. In the case of a monopolar device, the current flows through the patient to the return electrode in the manner previously described. In the case of bipolar devices operating in a conductive fluid environment, the return electrode is not in contact with tissue, but rather is submerged in the conductive fluid in the proximity of the active electrode. Current flow is from the active electrode through the conductive liquid and surrounding tissues to the return electrode of the bipolar device. Whether an electrode is monopolar or bipolar, current flows from all uninsulated surfaces of the active electrode to the return electrode anytime that the electrode is energized. This is in contrast to conventional surgery (also called "open surgery") in which current flows only through electrode surfaces in contact with the patient's tissue.

For an electrode in a fluid environment to vaporize tissue, as in the cutting process described previously, the current density at the electrode/tissue interface must be sufficiently high to cause arcing between the electrode and the patient. If such current density is not achieved, power flows from the active electrode to the return electrode with no desirable clinical effect. In fact, such current flow is highly undesirable since the current flowing from the active electrode heats the conductive fluid in the region surrounding the active electrode. A surgeon using a device which is energized but not arcing to the tissue may believe that he is not affecting tissue in close proximity to the active electrode, however, he may be subjecting the tissue to temperatures approaching 100° C. Even when the electrode is arcing to the tissue, the thermal effects are not limited to vaporization of the tissue. Appreciable undesirable heating of the fluid and tissue in the vicinity to the electrode takes place.

One way of avoiding the negative effects of the undesirable heating of the fluid and adjacent tissue structures is to set the power of the electrosurgical generator to a level that is low enough to minimize the heating of the liquid but high enough to produce sparks. There is an inherent difficulty, however, in satisfying acceptable electrosurgical parameters, since virtually all electrosurgical electrodes are "ignited," i.e., generate sparks, only when brought into contact with tissue, and then, generally, after a time delay of varying lengths. At the instant when sparks are not generated, most of the RF power supplied to an electrode operating in a conducting fluid is dissipated in the fluid itself as heat, consequently raising the temperature of the fluid within the joint and the adjacent tissue. At the instant when sparks are generated, the RF power is used for the creation of sparks in the vicinity of the electrodes. Therefore, energizing the electrosurgical electrode without initiation of sparks is dangerous and undesirable, as the heating may damage tissue structure uncontrollably in surrounding areas and also deep under the surface.

During the past several years, specialized arthroscopic electrosurgical electrodes also called ablators have been developed for arthroscopic surgery. The ablator electrodes differ from the conventional arthroscopic electrosurgical electrodes in that they are designed for the bulk removal of tissue by vaporization, rather than by cutting the tissue or coagulating the bleeding vessels. This way, during ablation, volumes of tissue are vaporized rather then discretely cut out and removed from the surgical site.

The power requirements of ablator electrodes are generally higher than those of other arthroscopic electrodes. The efficiency of the electrode design and the characteristics of the radio frequency (RF) power supplied to the electrode also affect the amount of power required for ablation. For example, electrodes with inefficient designs and/or powered by RF energy with poorly suited characteristics will require higher powers levels than those with efficient designs and appropriate generators. As a result of these factors, the ablation power levels of devices produced by different manufactures vary widely, with some manufactures using power levels significantly higher than those commonly used by arthroscopic surgeons. For example, ablator electrode systems from some manufacturers may use up to 280 Watts, significantly higher than the 30 to 70 Watt range generally used by other arthroscopic electrosurgical electrodes.

The amount of fluid temperature increase within a joint and, consequently, the temperature of the adjacent tissue is critical during the use of ablator electrodes. The fluid temperature may easily reach 45° C., at which cell death typically occurs, and this temperature is easily reached with high-powered ablators operating when sufficient flow is not used. The increase in the fluid temperature is also directly proportional to the increase in the power level. As such, the fluid temperature increases as the period of time necessary for an electrosurgical ablator to be energized increases. Standard arthroscopic electrosurgical electrodes are generally energized for only brief periods (generally measured in seconds) while specific tissue is resected or modified. In contrast, ablator electrodes are energized for longer periods of time (often measured in minutes) while volumes of tissue are vaporized.

During ablation, current flow from the ablator into the conductive fluid heats the fluid to its boiling point. Initially, steam bubbles form only at the edges of the ablator, but eventually they cover the entire surface of the electrode. The electrical resistance to current flow increases to its maximum value, maximum voltage is applied to the steam gap, and sparking occurs within the bubble. Sparking within the bubble destroys the tissue which is within the same bubble. After the tissue is destroyed, the sparking continues but no beneficial destruction takes place until new tissue is brought into contact with the active region of the probe. In practice, this is done by manual mechanical movement of the probe, which is conducted manually by the surgeon.

During the time when sparking does not occur, that is, when the emerging bubbles have not yet reached critical size or when sparking occurs without tissue in the active zone of the electrode, power is flowing from the electrode into the operating region without tissue being ablated. Furthermore, current flow into the fluid during this time causes heating of the fluid with no desirable clinical effect to the patient. Because no tissue is removed during this unproductively sparking or "non-sparking" period, an ablator operating with large unproductive time is inefficient. To achieve an acceptable rate of tissue ablation would require increasing the power supplied to the ablator. As discussed previously, however, increasing the power level increases the rate of heating of the fluid in the joint which, in turn, increases the likelihood of thermal injury to the patient.

Accordingly, there is a need to minimize the unproductive "non-sparking" or idle-sparking time of an electrosurgical ablator electrode to achieve improved tissue removal rates at low power levels. There is also a need for an electrosurgical ablator electrode of high efficiency with controlled vibrations or fast oscillating motion to minimize the "idle-sparking" time through moving the active zone of the probe to make contact with fresh tissue. A method of increasing the number of bubbles of critical size formed at the tip of the electrosurgical ablator electrode, as well as methods of fabricating such electrosurgical ablator electrode and methods of utilizing such ablator electrode in various electrosurgical procedures, are also needed.

BRIEF SUMMARY OF THE INVENTION

In one aspect, the invention provides a high efficiency electrosurgical ablator capable of producing a fast and slight vibratory or oscillatory motion. The electrosurgical ablator is linked to an element capable of imparting a vibratory or oscillatory motion to the ablator electrode. According to one embodiment, the electrosurgical ablator is linked to an oscillating circuit which affects the electrode electromechanically. The oscillating circuit may be provided external to the ablator or, in the alternative, within the handle of the ablator. In another embodiment, the electrosurgical ablator is connected to a piezoelectric element. The piezoelectric element may be provided external to the ablator or, in the alternative, within the handle of the ablator.

In another aspect, the invention provides an apparatus for conducting electrosurgical procedures or interventions comprising at least one vibrating electrosurgical probe that includes a shaft having a distal end and a proximal end. The distal end supports at least one vibrating ablator electrode. The proximal end is coupled to an element capable of imparting a vibrating and oscillatory motion, for example, an oscillating circuit or a piezoelectric element.

The invention also provides a method of employing an electrosurgical ablator in an electrosurgical procedure for which the total idle-sparking time (the time when sparking does not destroy tissue) is minimized when the ablator electrode is in contact with the tissue structure. The method comprises the steps of: (i) positioning an ablator electrode adjacent a target tissue, then (ii) either submerging the target tissue in an electrical conducting fluid or (iii) directing an electrically conducting fluid to the target tissue, and (iv) subjecting the ablator electrode to a vibrating and oscillatory motion to bring the active zone of the electrode to a region of fresh, yet undestroyed, tissue.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides a high efficiency electrosurgical ablator electrode capable of producing a fast and slight oscillatory motion. The electrosurgical ablator electrode is linked to an element capable of imparting a vibratory motion to the ablator electrode, for example, an oscillator or a piezoelectric element. As described in more detail below, the present invention contemplates the use of a single active electrosurgical electrode, or of an array of such active electrosurgical electrodes distributed over a distal surface of an electrosurgical probe, the electrosurgical electrode or electrodes being subjected to a vibratory or oscillatory motion.

Figure 1:
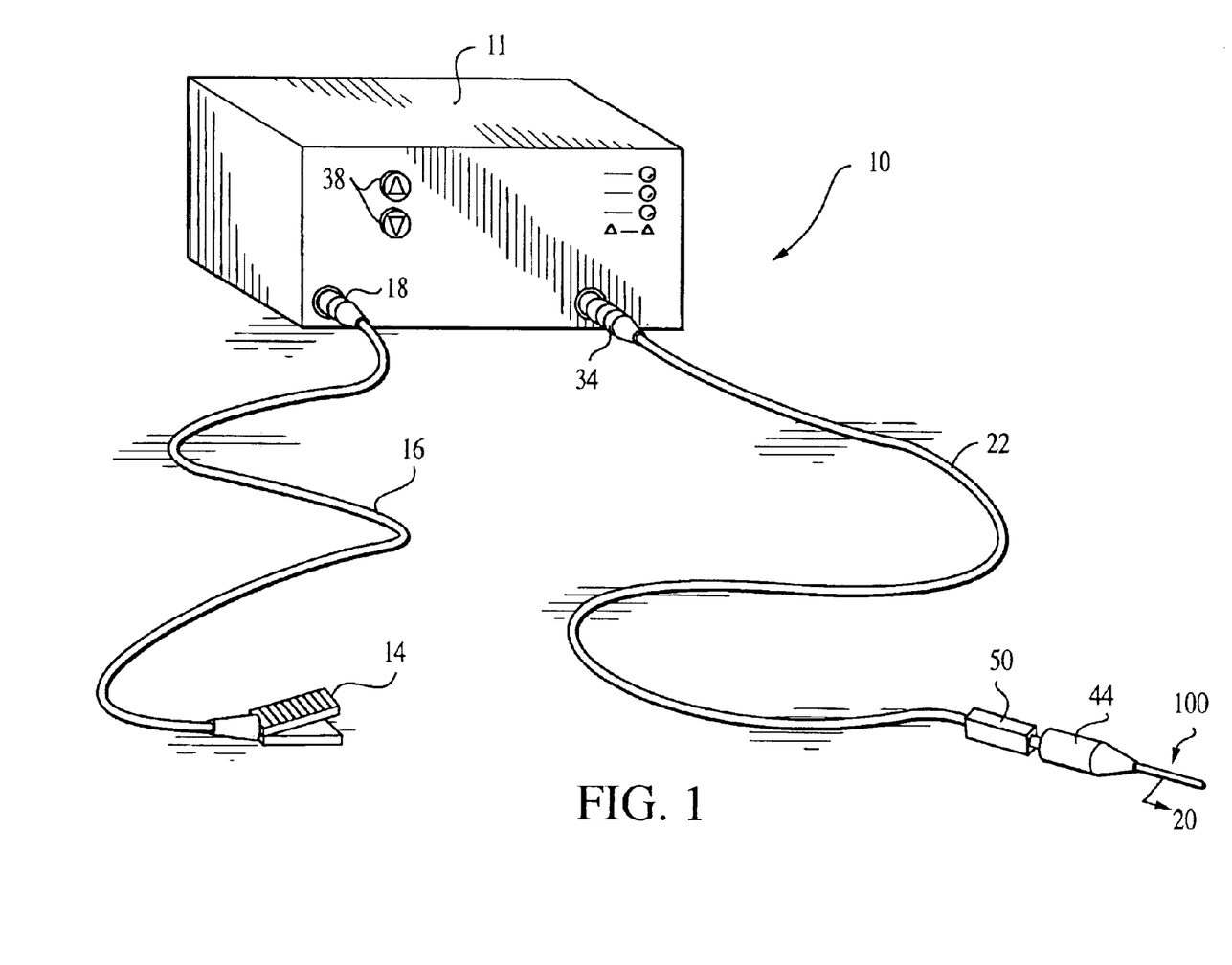
FIG. 1 is a perspective view of an electrosurgical system which includes an electrosurgical probe according to a first embodiment of the present invention.

Referring now to the drawings, where like elements are designated by like reference numerals, FIG. 1 illustrates a monopolar electrosurgical system 10 that employs a monopolar electrosurgical probe 100 of a first embodiment of the present invention. The monopolar electrosurgical system 10 of FIG. 1 may be used, for example, in the treatment of body tissue in minimally invasive procedures within the body, for example, in procedures that require the introduction of a surgical instrument through a percutaneous penetration or through a natural opening in the patient. Although, for simplicity, the invention will be described below with reference to a monopolar electrode, such as the monopolar electrosurgical electrode 20 (FIG. 2), the invention has equal applicability to systems employing bipolar electrosurgical electrodes.

As illustrated in FIG. 1, the monopolar electrosurgical system 10 includes an electrosurgical probe 100 that is connected to receptacle 34 of the electrosurgical power supply 11 by conductor cable 22. The electrosurgical probe 100 comprises a handle 44 provided with an oscillator 50 at its proximal end, and an electrosurgical electrode 20 at its distal end. Power supply 11 provides very high frequency or radio frequency (RF) voltage to the electrosurgical electrode 20. Power supply 11 is also provided with an operator-controllable voltage level adjustment 38 to control the applied voltage level. Thus, a surgeon or a medical operator may manually adjust the voltage level applied to electrosurgical electrode 20 through voltage level adjustment 38.

Power supply 11 of FIG. 1 also includes a foot pedal 14 which may be removably coupled to receptacle 18 through cable connector 16. The foot pedal 14 may be used to place the power supply into a predetermined operation mode, for example, into an "ablation" mode or a "coagulation" mode. In the "ablation" mode, a sufficient voltage is applied to the electrosurgical electrode 20 through voltage level adjustment 38 so that a plasma with sufficient energy is formed to dissociate or ablate the target tissue. The requisite voltage level depends on the number, size and spacing of the electrodes. Similarly, in the "coagulation" mode, a low enough voltage is applied to the electrosurgical electrode 20 so to avoid vaporization of the electrically conductive fluid.

Figure 2:
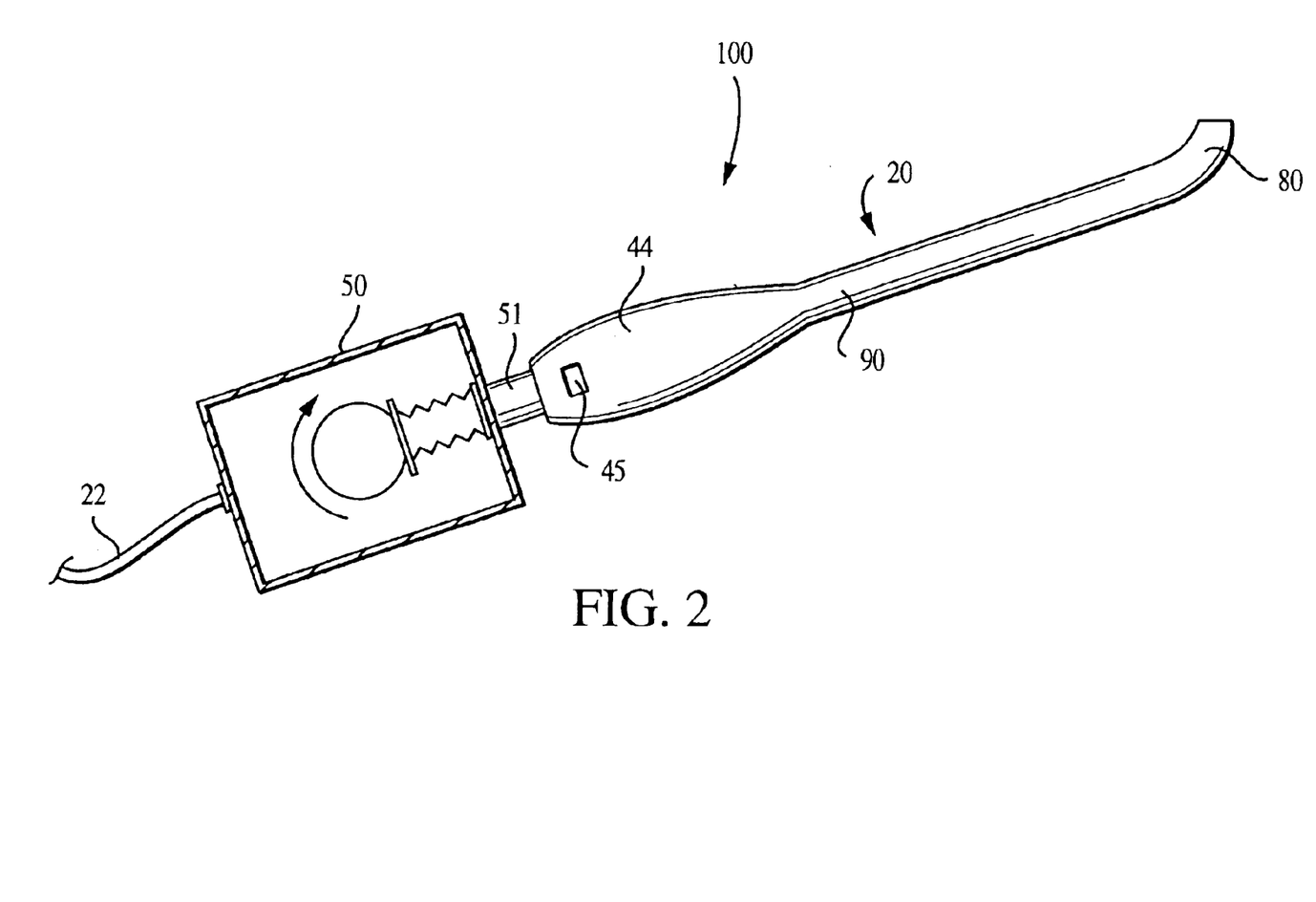
FIG. 2 is a perspective view of the electrosurgical probe of FIG. 1.

The electrosurgical probe 100 of FIG. 1 is illustrated in more detail in FIG. 2. The electrosurgical probe 100 comprises an elongated proximal shaft 90 having a proximal end adjacent the handle 44, and a distal end in contact with or near a distal active electrode 80. As shown in FIG. 2, vibrating member 51 driven electromechanically by the oscillator 50 matingly engages the proximal end of handle 44. This way, the electrosurgical ablator electrode 20 is coupled to the source of vibrational energy 51 driven by the oscillator 50 operating in the range of 2 to 5,000 oscillations per second, more preferably of about 2 to 1,000 oscillations per second.

These low frequency vibrations are controlled by means 45 (FIG. 2) located within or on the handle 44. The low frequency vibrations transmit along the elongated proximal shaft 90 and to the distal active electrode 80 providing a mechanical motion of the tip of the distal active electrode 80. The mechanical motion of the tip of the distal active electrode 80 may be in the direction of the long axis of the electrosurgical probe 100. Alternatively, oscillating element 51 may electromechanically cause a rotation in a back and forth motion along the wall of the elongated proximal shaft 90 which is translated to the tip of the distal active electrode 80. Oscillator 50 may be also provided with elements that can electromechanically impart oscillatory motion of varying magnitude and nature. In addition, oscillator 50 may comprise adjusting means which may provide any combination of linear and pendulum oscillatory motion to the distal active electrode 80.

The elongated proximal shaft 90 of FIG. 2 may have a variety of configurations for mechanically supporting the distal active electrode 80 and permitting a treating physician to manipulate the distal active electrode 80 having a vibrating or oscillatory motion from a proximal end of the shaft. As such, the elongated proximal shaft 90 may be a tube or a narrow-diameter rod of dimensions that permit the distal active electrode 80 to be introduced through an associated cannula in a minimally invasive procedure, such as arthroscopic or other endoscopic procedures, or into a body cavity, such as the mouth or the abdominal cavity.

The elongated proximal shaft 90 may have a length of about at least 10 cm, more preferably of about 10 to about 100 cm, and a diameter of at least 1 mm, more preferably of about 2 to 10 mm. The elongated proximal shaft 90 may be flexible or rigid, or may be formed as a combination of a flexible shaft combined with a generally rigid external tube for increased mechanical and physical support. The elongated proximal shaft 90 may also include pull wires or shape memory actuators or other known mechanisms for facilitating the positioning of the distal active electrode 80 in the vicinity of the target tissue. In addition, the elongated proximal shaft 90 may include other conductive elements and wires that run axially through the shaft and permit connection of the distal active electrode 80 to a connector at the distal end of the elongated proximal shaft 90.

The distal active electrode 80 (FIG. 2) of the electrosurgical probe 100 having a vibrating or oscillatory motion comprises a dielectric material covering and insulating a metallic body region, and a metallic tip located at the distal end of the metallic region. The dielectric material may comprise an electrically insulating material such as epoxy, plastic, silicon-based material, ceramic, glass or compositions of these mentioned materials, among many others. The dielectric material may also comprise a perforated shield also formed of an electrically insulating material which may be porous and which may include an opening that allows an electrically conductive liquid, for example an isotonic saline solution, to contact the metallic tip and the target tissue.

The metallic body region and the metallic tip located at the proximal end of the metallic region may have various cross-sectional shapes and geometries, for example, cylindrical, rectangular, or elipsoidal, among many others. The metallic body region and the metallic tip may be formed of electrically conductive materials such as metals and metal alloys, for example, stainless steel and stainless steel alloys, platinum and platinum alloys, gold and gold alloys, nickel and nickel alloys, titanium and titanium alloys, and molybdenum and molybdenum alloys, among others. Sufficient clearance exists between the inner surface of dielectric material and outer surface of metallic body region to allow thermal expansion of the metallic body without cracking the dielectric material, particularly at the distal end of the items. The metallic body region may be bonded to the dielectric material by a sealing material which is typically an inorganic sealing that provides effective electrical insulation and good adhesion to both the dielectric material and the metallic body region. The sealing material may preferably have a compatible thermal expansion coefficient and a melting point above the temperature reached in the region during use.

Although, for simplicity, the embodiments of the present invention will be described below with reference to only one distal active electrode 80 having a vibratory or oscillatory motion as part of the electrosurgical probe 100, the invention is not limited to this exemplary embodiment. Accordingly, the invention also contemplates the formation of a plurality of such distal active electrodes 80 as part of an electrosurgical electrode.

Figure 3:
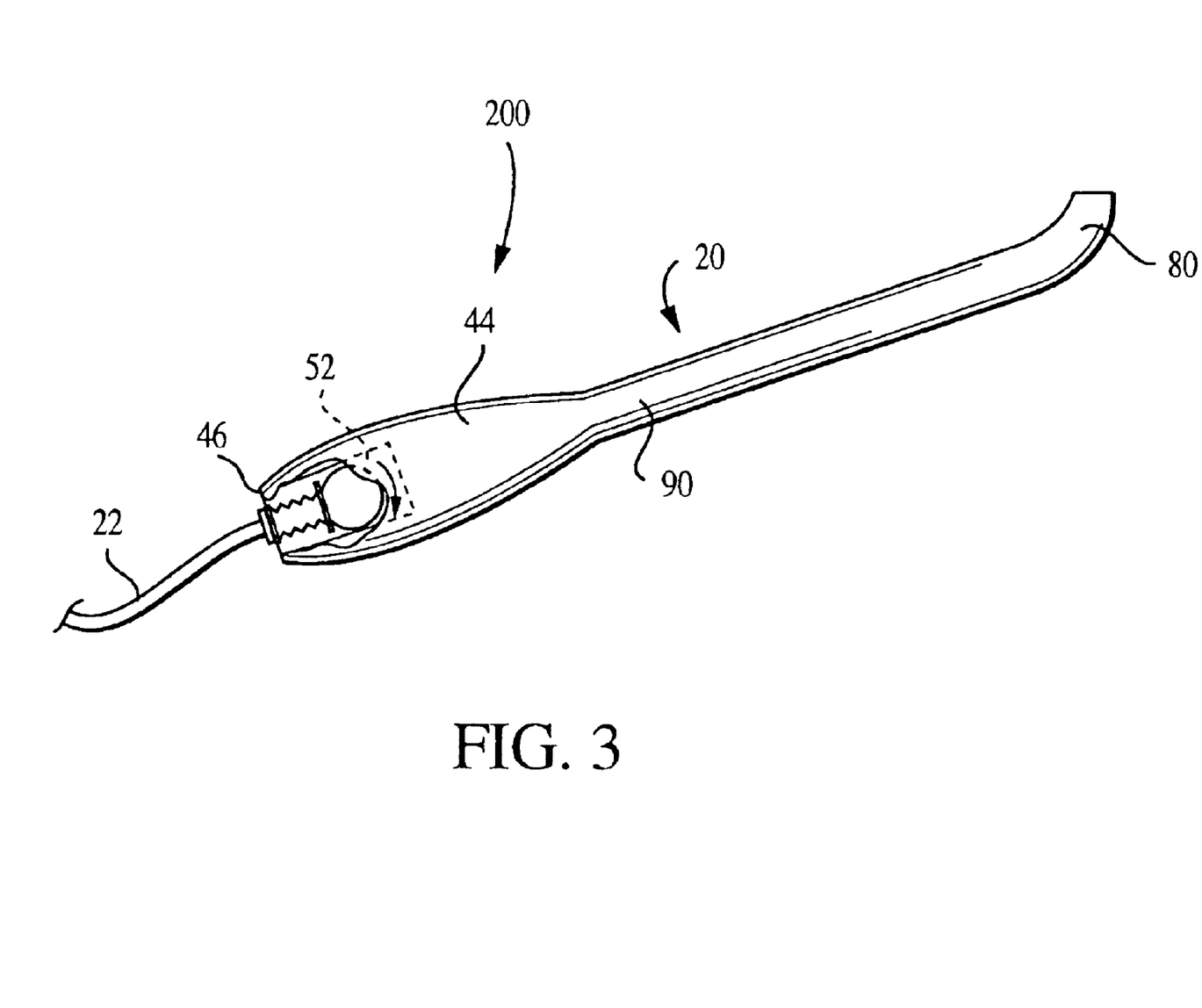
FIG. 3 is a perspective view of an electrosurgical probe according to a second embodiment of the present invention.

FIG. 3 illustrates another embodiment of the present invention, according to which electrosurgical probe 200 comprises a handle 44 and an oscillator 52 located within the handle 44, rather than external to it, as in the first embodiment. As shown in FIG. 3, proximal end 46 of handle 44 is in direct contact with, and is driven by, the oscillator 52. This way, the electrosurgical ablator electrode 20 is coupled to a source of vibrational energy driven by the oscillator 52 operating in the range of 2 to 5,000 oscillations per second, more preferably of about 2 to 100 oscillations per second. These low frequency vibrations transmit along the elongated proximal shaft 90 and to the distal active electrode 80, further imparting a mechanical vibratory motion of the tip of the distal active electrode 80. The mechanical motion of the tip of the distal active electrode 80 may be in the direction of the long axis of the electrosurgical probe 100.

Figure 4:
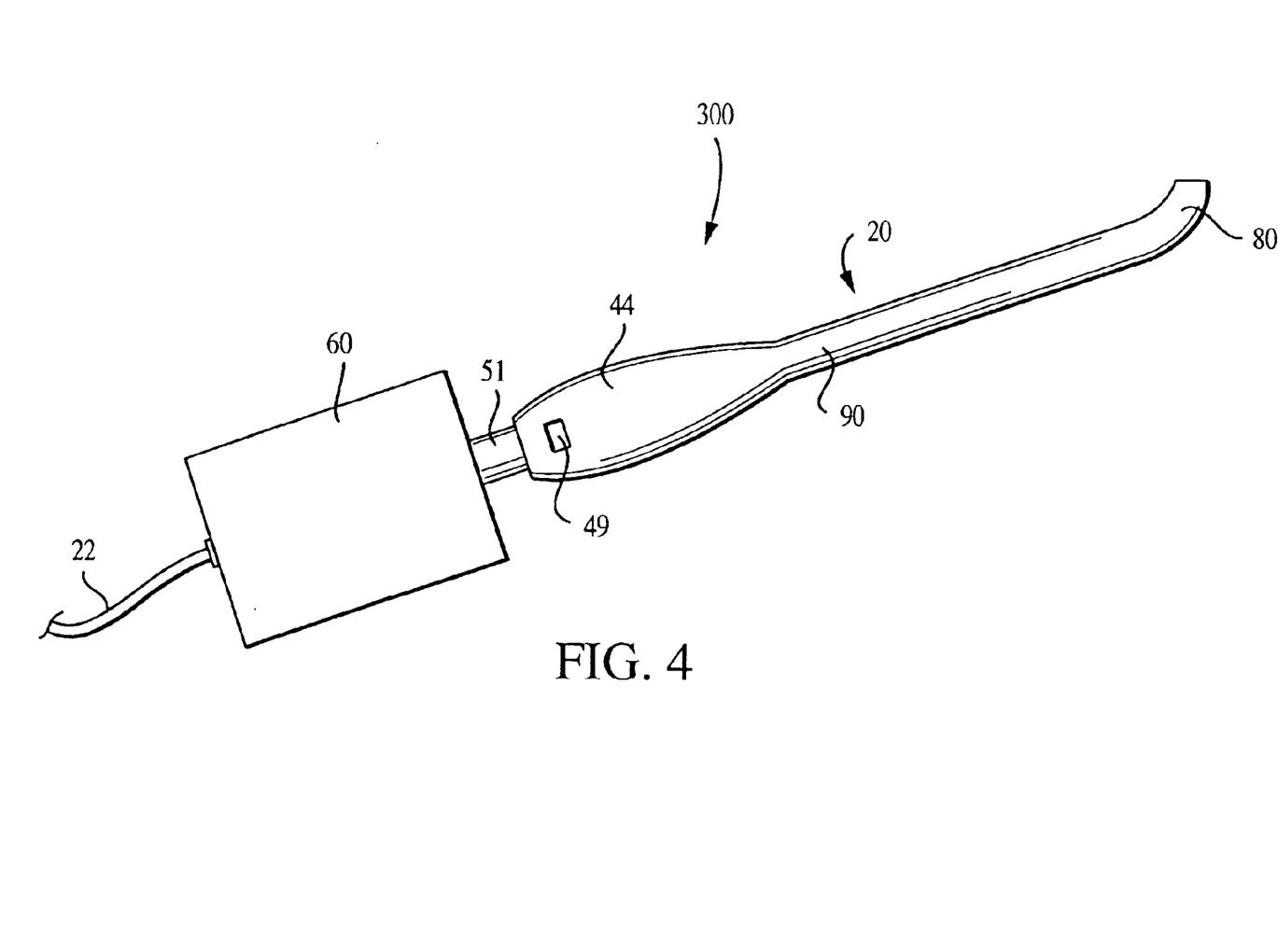
FIG. 4 is a perspective view of an electrosurgical probe according to a third embodiment of the present invention.
Figure 5:
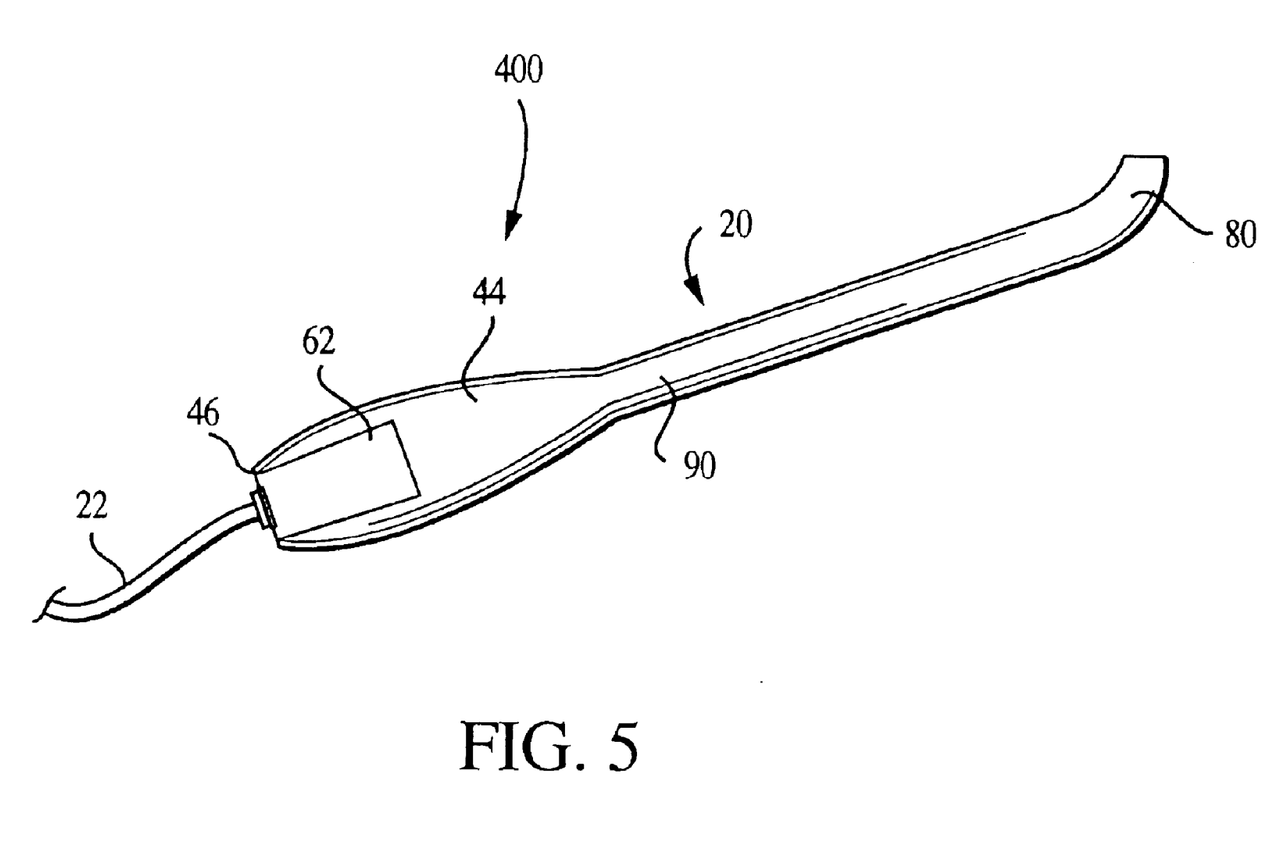
FIG. 5 is a perspective view of an electrosurgical probe according to a fourth embodiment of the present invention.

FIGS. 4–7 illustrate yet other embodiments of the present invention. FIGS. 4 and 5, for example, illustrate electrosurgical probes 300, 400 include piezoelectric devices 60, 62 provided in contact with the handle 44 and located external or internal to the handle 44, respectively. FIG. 4 depicts piezoelectric device 60 located external relative to the handle 44 and excited by an electronic circuit 49 (FIG. 4) located within the handle 44 and powered by a battery located within the handle 44. FIG. 5 illustrates piezoelectric device 62 located within the handle 44.

As known in the art, piezoelectric elements such as piezoelectric devices 60, 62 of FIGS. 4–5 operate based upon the piezoelectric effect. Details on the fabrication and function of piezoelectric devices may be found, for example, in U.S. Pat. No. 6,335,586 to Takeuchi et al., the disclosure of which is incorporated by reference herein. Although FIG. 4 illustrates the electronic circuit 49 and although the above embodiments have been described with reference to an operating battery located within the handle 44, the invention is not limited to these embodiments. Accordingly, the present invention also contemplates electrosurgical probes including piezoelectric devices that are excited by electronic circuits located external to the handle 44, as well as electrosurgical probes including piezoelectric devices that are excited by electronic circuits and powered by external power supplies, which are all located external to the handle 44.

Figure 6:
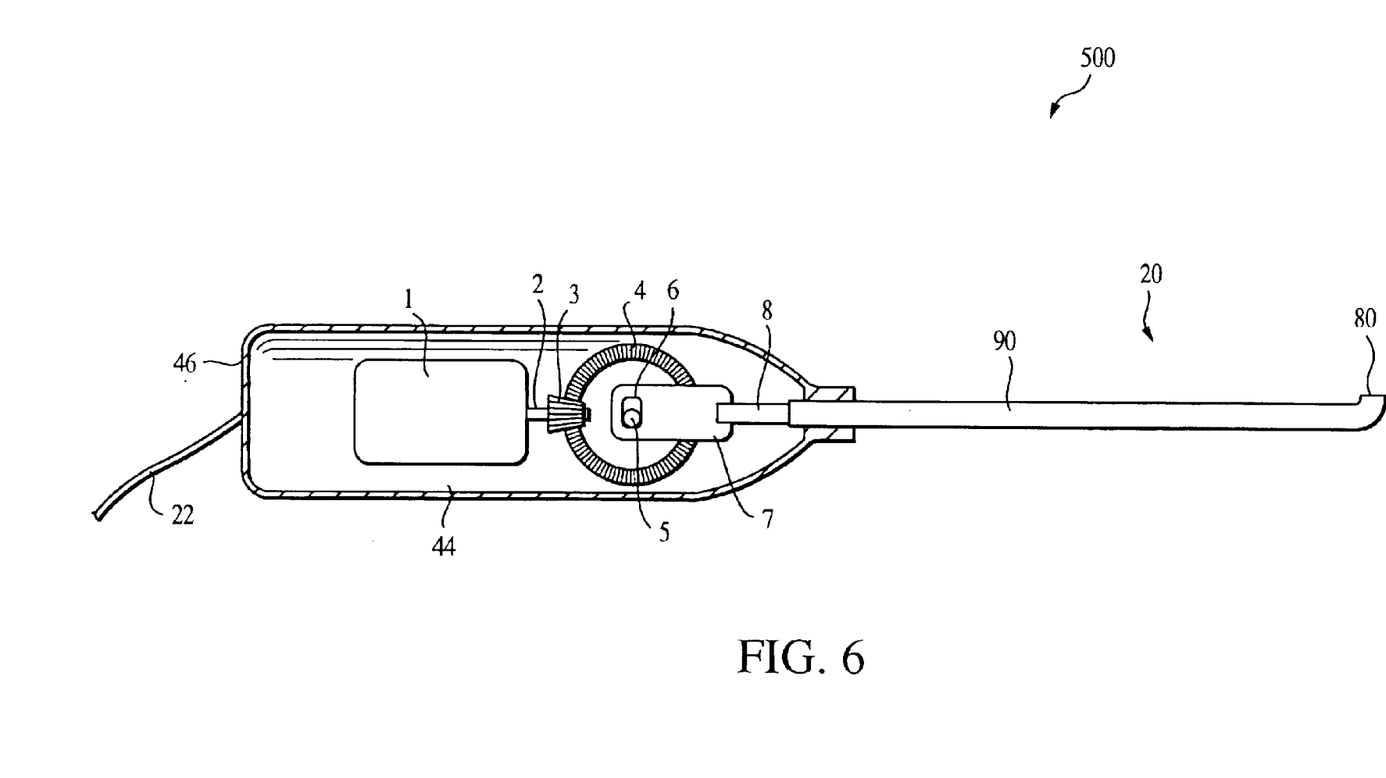
FIG. 6 is an enlarged cross-sectional diagrammatic view of an electrosurgical probe according to a fifth embodiment of the present invention.
Figure 7A:
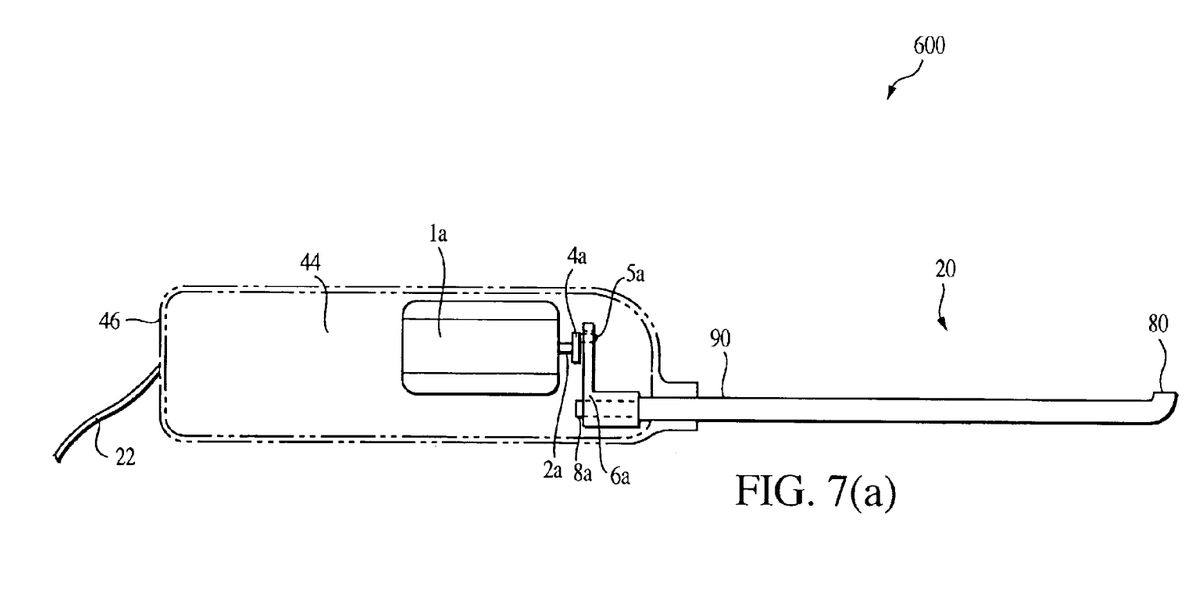
FIGS. 7a–b illustrate an enlarged cross-sectional view and a top planar view, respectively, of an electrosurgical probe according to a sixth embodiment of the present invention.
Figure 7B:
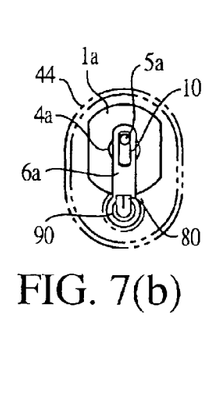

FIGS. 6 and 7a–b illustrate other embodiments of the present invention according to which electrosurgical probes 500, 600 include electrical motors 1, 1a located internal to the handle 44 and imparting an axial oscillatory motion and an angular oscillatory motion, respectively, upon the active electrode 80. FIG. 6 illustrates electrical motor 1 including an output shaft 2 with a pinion gear 3 attached to it. The pinion gear 3 engages ring gear 4 so that energizing motor 1 causes ring gear 4 to rotate, the speed of rotation being equal to the motor speed multiplied by the ratio of the number of teeth of the pinion gear 3 to ring gear 4. Ring gear 4 has an axial pin 5 mounted eccentrically to the gears center of rotation. The axial pin 5 engages a slot 6 in mechanical connector 7 so that rotational motion of ring gear 4 is translated to axial oscillatory motion of the connector 7 and to electrode rod 8. The electrode rod 8 is movably constrained within the elongated proximal shaft 90 mounted to handle 44. Axial oscillation of the electrode rod 8 is transferred to the active electrode 80 which is mechanically mounted thereto.

FIG. 7a illustrates electrical motor 1a located within the handle 44. Output shaft 2a of the motor 1a is located parallel to the axis of electrode rod 8a and the elongated proximal shaft 90 is mounted to handle 44. The output shaft 2a has a drive element 4a attached to it. As illustrated in FIGS. 7a–b, the drive element 4a has an eccentrically mounted pin 5a protruding from its distal surface, the axis of the pin 5a being parallel to the axis of the output shaft 2a. The eccentrically mounted pin 5a engages slot 10 in link 6, the opposite end of link 6 being nonrotatably attached to the proximal end of the electrode rod 8a. The electrode rod 8a is rotatably confined within the elongated proximal shaft 90 such that oscillatory motion, which is imparted to the rod 8a by link 6 due to pin 5a acting on slot 10 during rotation of the motor, is transferred to the active electrode 80.

Although the above embodiments have been described with reference to an oscillating circuit, a piezoelectric device or a motor that is capable of imparting a vibratory motion on the tip of the electrosurgical ablator electrode 20 of the present invention, the invention is not limited to the above-described embodiments. Accordingly, the present invention also contemplates an electrosurgical probe linked to other means of imparting a vibratory or oscillatory motion, for example, mechanical means attached to the distal active electrode 80 of the electrosurgical ablator electrode 20 and powered by a gear mechanism driven by a motor, for example, which may be located within the handle 44. The gear mechanism may be further mounted within handle 44 and may be powered by a battery within the handle 44, or alternatively, by an external power supply. The gear mechanism may be also attached external to the handle 44 and to the distal active electrode 80, and may also be powered by either a battery or an external power supply.

The present invention also contemplates imparting a vibratory or oscillatory motion to the distal active electrode 80 of the electrosurgical ablator electrode 20 by employing an eccentric weight affixed to the output shaft of an electric motor, which may be located within handle 44, for example. As in the previous embodiments, the electric motor may be powered and operated by a battery located within the handle 44 or by an external power supply. A vibrating magnetic mechanism, or an ultrasound mechanism or a pneumatic mechanism may be also employed to impart a vibratory or oscillatory motion to the distal active electrode 80 of the electrosurgical ablator electrode 20.

The electrosurgical electrode of the present invention described above with reference to FIGS. 1–7 may be employed in various electrosurgical procedures for which the "non-sparking" time of the electrosurgical ablator is minimized. For example, the electrosurgical probe 100 (FIGS. 1–2) of the first embodiment of the present invention may be employed in a variety of surgical medical procedures in the presence of an electrically conductive fluid to remove and/or modify a particular target tissue. Accordingly, the electrosurgical probe 100 of the of the present invention including oscillator 50 attached external to the handle 44 may be used in a conventional open surgery environment or in other, less invasive, techniques that use cannulas or various port access devices if conductive fluid is present. The present invention has also applications in surgical procedures where the target tissue is flooded with, or submerged in, an electrically conductive fluid such as in many arthroscopic procedures for ablation, coagulation, shaping and cutting of various body parts such as the knee, shoulder, hip, ankle, elbow, hand or foot.

The present invention has also equal applicability to surgical procedures where the target tissue is flooded with a natural conductive fluid of the human body, such as blood or lymphatic plasma, for example, which act as electrically conductive fluids. Nevertheless, an electrically conductive fluid introduced into the patient's body is preferred over blood because blood tends to coagulate at certain temperatures. In addition, the patient's blood or plasma may lack the necessary conductivity to adequately carry out the particular electrosurgical procedure desired.

Surgical procedures using the electrosurgical probe 100 of the invention include introducing the electrode assembly in close proximity to the surgical site through an artificial conduit or a cannula, or through a natural conduit which may be in an anatomical body cavity or space or one created surgically. The cavity or space may be distended during the procedure using a fluid or may be naturally held open by anatomical structures. In addition, the surgical site may be bathed in a continuous flow of conductive fluid, such as saline solution, to fill and distend the cavity. The procedures may include simultaneous viewing of the site via an endoscope or using an indirect visualization means.

Figure 8:
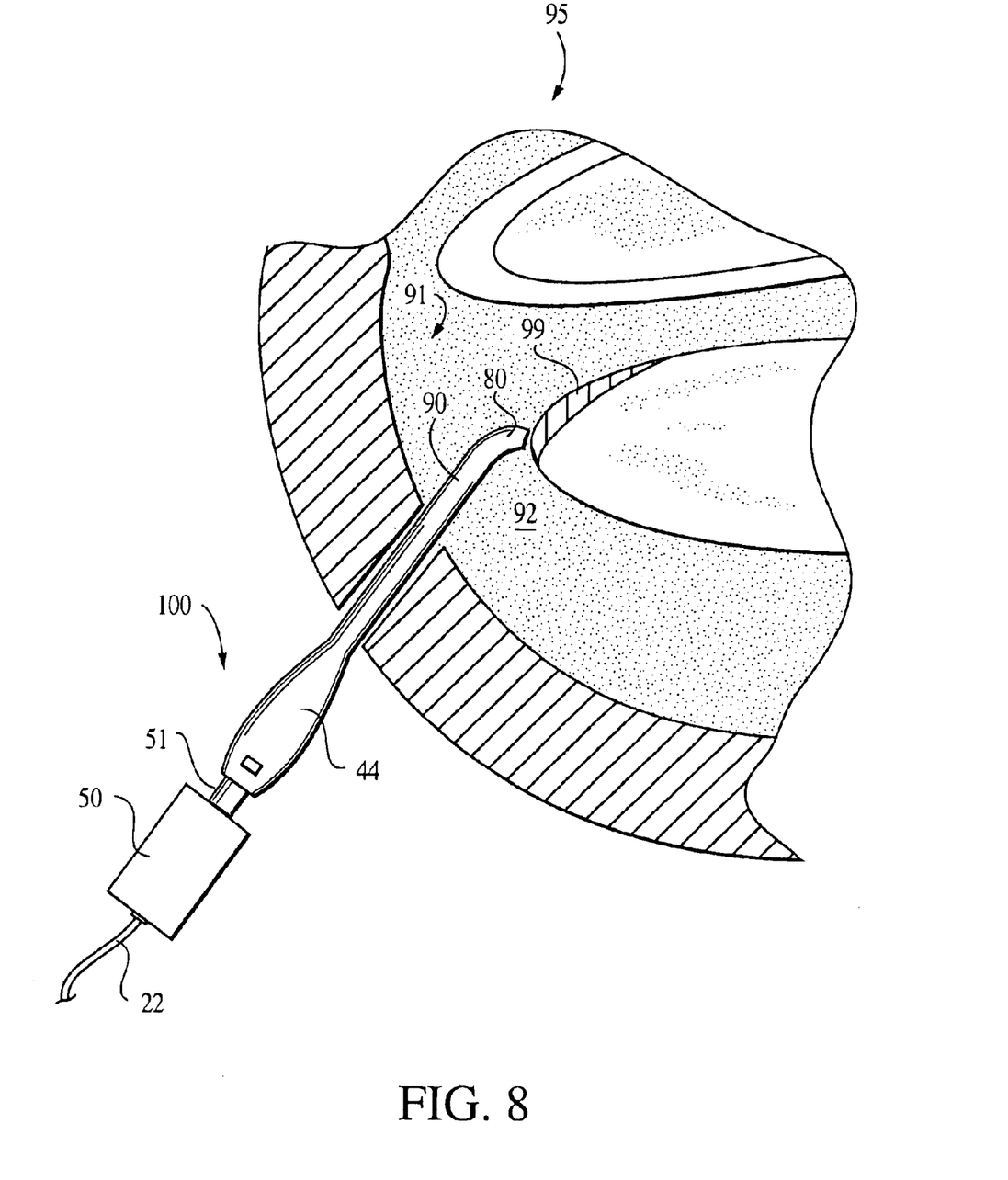
FIG. 8 is a schematic cross-sectional view of a knee joint undergoing an electrosurgical procedure employing an electrosurgical probe of the present invention.

To better illustrate an exemplary surgical procedure conducted with the electrosurgical probe 100 of the present invention, reference is now made to FIG. 8, which illustrates a schematic cross-sectional view of a knee joint region 95. The knee joint region 95 of FIG. 8 may undergo an arthroscopic procedure, for example, with electrosurgical probe 100 having electrosurgical ablator electrode 20 provided with a vibratory or oscillatory motion by oscillator 50, and in accordance with the first embodiment of the present invention.

As known in the art, an endoscope (not shown) may be provided at one end with the distal active electrode 80, and then introduced into knee cavity 92 (FIG. 8) containing electrically conductive fluid 91 (FIG. 8) and in close proximity to target tissue 99 (FIG. 8). If the target tissue 99 of the knee joint region 95 is a damaged meniscus, for example, then target tissue 99 may undergo a partial or complete electrosurgical meniscectomy using distal active electrode 80. Alternatively, the endoscope may be introduced separately from the electrosurgical electrode 80, via separate access means in a surgical technique commonly known as triangulation. In any event, knee cavity 92 may be distended during the arthroscopic procedure using electrically conductive fluid 91, so that target tissue 99 may be bathed in a continuous flow of conductive fluid 91, which may be preferably a saline solution.

Once distal active electrode 80 is positioned in the proximity of the target tissue 99 and the target tissue 99 is submerged in the electrically conductive fluid 91, the electrosurgical probe 100 is energized by the electrosurgery power supply 11 (FIG. 1). The power supply delivers radio frequency energy, typically in the range of 100 kHz to 3 MHz, through the cable system 22 (FIGS. 1 and 8) to the electrosurgical ablator electrode 20 and further to the distal active electrode 80.

Figure 9:
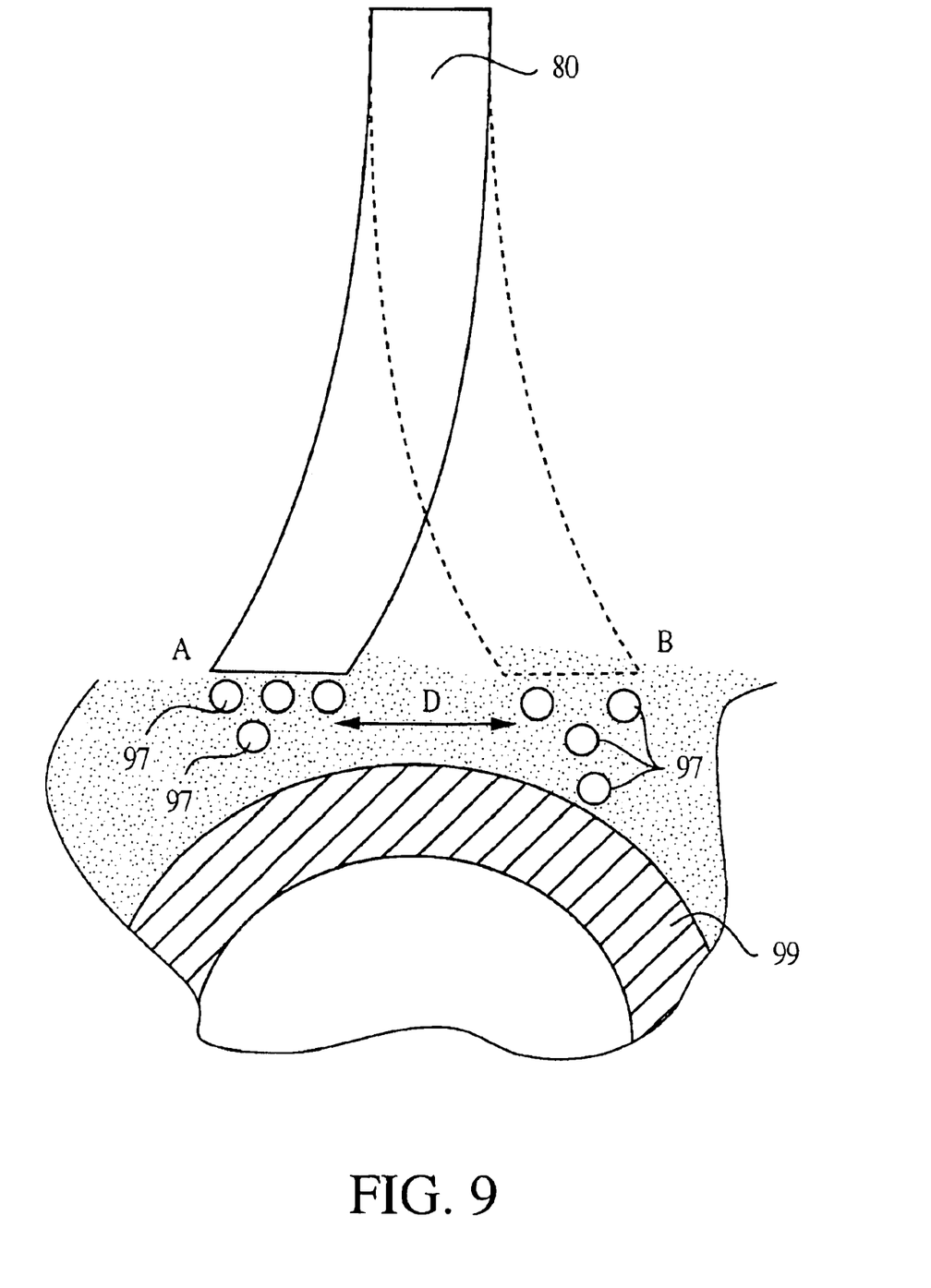
FIG. 9 is an enlarged cross-sectional view of the electrosurgical ablator electrode of the first embodiment of the present invention in proximity to a target tissue of the structure of FIG. 8.

For a better understanding of the phenomenas that occur when the distal active electrode 80 is energized by power supply 11 and is subjected to a vibratory motion in the proximity of, or in contact with, the target tissue 99, reference is made to FIG. 9. FIG. 9 illustrates an enlarged cross-sectional view of the tip of the distal active electrode 80 in the proximity of the target tissue 99 of the knee joint region 95.

Initially, and at the point when the distal active electrode 80 is located in sparking region A of FIG. 9, the high radio frequency energy is dissipated in the electrically conductive fluid 91 and is directed toward the target tissue 99. As a result of the dissipation of the high radio frequency energy in the electrically conductive fluid 91, the conductive fluid 91 is heated to a boiling point so that steam bubbles 97 form in region A and only near the metal tip 46 of the distal active electrode 80. As the radio frequency energy continues to dissipate, the steam bubbles 97 grow and cover other parts of the distal active electrode 80 so that, when steam bubbles reach a critical size, sparking occurs within the bubbles. However, sparking ceases when the bubbles grow too large and become oversized, or when the oversized bubbles have not been removed from the distal active electrode 80 to allow new bubbles to grow and spark.

Accordingly, once the sparking conditions in region A become unfavorable, that is, when the "non-sparking" period starts in region A, the oscillator 50 is activated so that the distal active electrode 80 vibrates and moves a distance "D" from region A to region B (FIG. 9). The distance D may vary according to the parameters of the element imparting a vibratory or oscillatory motion, in this case oscillator 50, and may be about 0.1 to about 5 millimeters. In region B, new steam bubbles 97 form at the metal tip 46 of the distal active electrode 80 also as a result of the dissipation of the high radio frequency energy in the electrically conductive fluid 91 and of the heating of fluid 91. As the radio frequency energy continues to dissipate, the steam bubbles 97 located in sparking region B cover other parts of the distal active electrode 80 so that, when steam bubbles reach a critical size in region B, sparking occurs within the bubbles destroying the tissue inside the bubble or active region.

Once the tissue in the sparking region B is mostly destroyed and further sparking does not destroy any additional tissue in this region, the distal active electrode 80 of the electrosurgical probe 100 may subsequently oscillate to another sparking region, or back to the sparking region A, so that new tissue will be subjected to destruction. Thus, as a result of decreasing the "low-efficiency sparking" time period during which power is dissipated with no clinical benefit to the patient, an increased ablation rate is achieved without increasing the power level.

Although the present invention has been described above with reference to arthroscopic surgery of a knee joint structure, the invention is not limited to the above embodiments. Accordingly, the electrosurgical electrode 20 (FIGS. 1–7) having a vibratory or oscillatory motion may be employed for a variety of arthroscopic procedures, for example, in the dissection, resection, vaporization, desiccation and coagulation of tissue structures in various endoscopic and percutaneous procedures performed on joints of the body including, but not limited to, spinal and other non-synovial joint techniques.

Arthroscopic procedures encompassed by the present invention may further include: lateral retinacular release of the knee joint; removal of anterior and posterior cruciate ligaments; labral tear resection; acromioplasty, bursectomy and subacromial decompression of the shoulder joint; anterior release of the tempomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of disc prolapse or as part of a spinal fusion via a posterior or anterior approach to the cervical, thoracic and lumbar spine or any other fibrous joint for similar purposes; excision of diseased tissue and haemostasis, among others.

The vibrating electrosurgical electrode 20 (FIGS. 1–7) of the present invention may be also used in hysteroscopic surgical procedures or urological endoscopic (urethroscopy, cystoscopy, ureteroscopy and nephroscopy) and percutaneous interventions. Hysteroscopic procedures may include: removal of submucosal fibroids, polyps and malignant neoplasms; resection of congenital uterine anomalies such as a septum or subseptum; division of synechiae (adhesiolysis); ablation of diseased or hypertrophic endometrial tissue; and haemostasis. Urological procedures may include: electrovaporization of the prostate gland (EVAP) and other similar procedures commonly referred to as transurethral resection of the prostate (TURP) including, but not limited to, interstitial ablation of the prostate gland by a percutaneous or perurethral route whether performed for benign or malignant disease; transurethaal or percutaneous resection of urinary tract tumors; division of strictures as they may arise at the pelviureteric junction (PUJ), ureter, ureteral orifice, bladder neck or urethra; correction of ureterocoele, among others.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of conducting an electrosurgical procedure comprising the steps of:

providing a single active electrode of a monopolar electrosurgical probe;

providing an electrically conductive fluid in the proximity of a tissue to be treated;

positioning said single active electrode in a first region located in the proximity of said tissue to be treated in the presence of said electrically conductive fluid;

applying a high frequency voltage to said single active electrode to generate an electric field and current adjacent said single active electrode;

effecting ablation of at least a portion of said tissue to be treated in said first region; and imparting a vibratory motion of about 2 to about 5,000 oscillations per second to said single active electrode so as to rapidly and alternately reposition said single active electrode between said first region and a second region located in the proximity of said tissue to be treated in the presence of said electrically conductive fluid, to manage the formation of bubble formation bubbles at said single active electrode to facilitate tissue vaporization in said electrically conductive fluid.

2. The method of claim 1, wherein said step of imparting a vibratory motion to said active electrode includes connecting said active electrode electromechanically to an oscillator.

3. The method of claim 1, wherein said step of imparting a vibratory motion to said active electrode includes connecting said active electrode electromechanically to a piezoelectric element.

4. The method of claim 1, wherein said step of imparting a vibratory motion to said active electrode includes connecting said active electrode electromechanically to a gear mechanism.

5. A method of reducing the non-sparking time of a mononopolar electrosurgical ablator for use in a monopolar electrosurgical procedure, said method comprising:

providing an electrically conductive fluid in the proximity of a tissue to be treated;

positioning an a single active electrode of said monopolar electrosurgical ablator in a first region of said tissue to be treated in the presence of said electrically conductive fluid;

applying a high frequency voltage to said single active electrode to generate an electric field and current adjacent said first region;

imparting a vibratory motion to said single active electrode so as to rapidly and alternately reposition said single active electrode between said first region and a second region located in the proximity of said tissue to be treated in the presence of said electrically conductive fluid; and applying a high frequency voltage to said single active electrode to generate an electric field and current adjacent said second region and to manage bubble formation at said single active electrode to facilitate tissue vaporization in said electrically conductive fluid.

6. The method of claim 5, wherein said step of imparting a vibratory motion to said active electrode includes connecting said active electrode to an oscillator.

7. The method of claim 5, wherein said step of imparting a vibratory motion to said active electrode further includes connecting said active electrode to a piezoelectric element.

8. The method of claim 5, wherein said step of imparting a vibratory motion to said active electrode includes connecting said active electrode to a gear mechanism.

* * * * *